United States Patent
Krieg et al.

(10) Patent No.: US 7,522,952 B2
(45) Date of Patent: Apr. 21, 2009

(54) COMBINED POSITRON EMISSION TOMOGRAPHY AND MAGNETIC RESONANCE TOMOGRAPHY UNIT

(75) Inventors: Robert Krieg, Nuremberg (DE); Rainer Kuth, Herzogenaurach (DE); Ralf Ladebeck, Erlangen (DE); Ralph Oppelt, Uttenreuth (DE); Wolfgang Renz, Erlangen (DE); Sebastian Schmidt, Erlangen (DE); Markus Vester, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 162 days.

(21) Appl. No.: 11/395,267

(22) Filed: Apr. 3, 2006

(65) Prior Publication Data

US 2006/0251312 A1    Nov. 9, 2006

(30) Foreign Application Priority Data

Apr. 1, 2005    (DE) .................... 10 2005 015 070

(51) Int. Cl.
*A61B 5/055* (2006.01)
(52) U.S. Cl. .................... 600/411; 600/427; 600/436; 324/318; 324/322; 250/363.03
(58) Field of Classification Search ........... 600/411, 600/427, 436; 324/300, 318, 322; 250/363.03, 250/363.04
See application file for complete search history.

(56) References Cited

U.S. PATENT DOCUMENTS

| | | | | |
|---|---|---|---|---|
| 4,825,163 A | * | 4/1989 | Yabusaki et al. | 324/318 |
| 4,939,464 A | * | 7/1990 | Hammer | 324/318 |
| 5,217,010 A | * | 6/1993 | Tsitlik et al. | 607/9 |
| 5,719,400 A | * | 2/1998 | Cherry et al. | 250/368 |
| 6,060,883 A | * | 5/2000 | Knuttel | 324/318 |
| 6,631,284 B2 | * | 10/2003 | Nutt et al. | 600/427 |
| 6,888,153 B2 | * | 5/2005 | Hayes | 250/515.1 |

(Continued)

FOREIGN PATENT DOCUMENTS

DE    44 14 371 A1  *  1/1994

(Continued)

OTHER PUBLICATIONS

D. Schlyer et al., "Development of a Simultaneous PET/MRI Scanner" Nuclear Science Symposium Conference Record 2004, Oct. 16-22, 2004, vol. 4., pp. 3419-3421.

*Primary Examiner*—Ruth S Smith
*Assistant Examiner*—Jonathan G Cwern
(74) *Attorney, Agent, or Firm*—Staas & Halsey LLP

(57) ABSTRACT

A combined PET/MRI tomography unit has a PET unit with a unit part assigned to the examination space, and a first evaluation unit for evaluating the PET electric signals. The unit part has a gamma ray detector. The combined unit has an MRI unit and a second evaluation unit for evaluating MRI signals. The MRI unit has a high frequency antenna as well as a gradient coil system, the high frequency antenna device being arranged nearer to the examination space than the gradient coil system, as well as a high frequency shield arranged between the gradient coil system and the high frequency antenna device. The PET unit part is arranged between the high frequency shield and the high frequency antenna device. A shielding cover for the high frequency antenna device faces the high frequency antenna device. The shielding cover is opaque to high frequency radiation.

20 Claims, 3 Drawing Sheets

U.S. PATENT DOCUMENTS

| | | | |
|---|---|---|---|
| 6,930,482 B2* | 8/2005 | Heid et al. | 324/318 |
| 6,946,841 B2* | 9/2005 | Rubashov | 324/318 |
| 7,068,035 B2* | 6/2006 | Nistler et al. | 324/322 |
| 7,218,112 B2* | 5/2007 | Ladebeck et al. | 324/318 |
| 7,267,661 B2* | 9/2007 | Susi | 604/67 |
| 7,282,916 B2* | 10/2007 | Eberlein et al. | 324/318 |
| 2003/0090267 A1* | 5/2003 | Rubashov | 324/318 |
| 2003/0105397 A1* | 6/2003 | Tumer et al. | 600/436 |
| 2004/0092809 A1* | 5/2004 | DeCharms | 600/410 |
| 2004/0236209 A1* | 11/2004 | Misic et al. | 600/423 |
| 2005/0113667 A1* | 5/2005 | Schlyer et al. | 600/411 |
| 2006/0052685 A1* | 3/2006 | Cho et al. | 600/407 |
| 2006/0250133 A1* | 11/2006 | Krieg et al. | 324/318 |
| 2006/0251312 A1* | 11/2006 | Krieg et al. | 382/131 |
| 2006/0293580 A1* | 12/2006 | Ladebeck et al. | 600/407 |

FOREIGN PATENT DOCUMENTS

| | | |
|---|---|---|
| DE | 44 14 371 | 7/1995 |
| EP | 141 383 | 8/1989 |
| EP | 177 855 | 6/1991 |

* cited by examiner

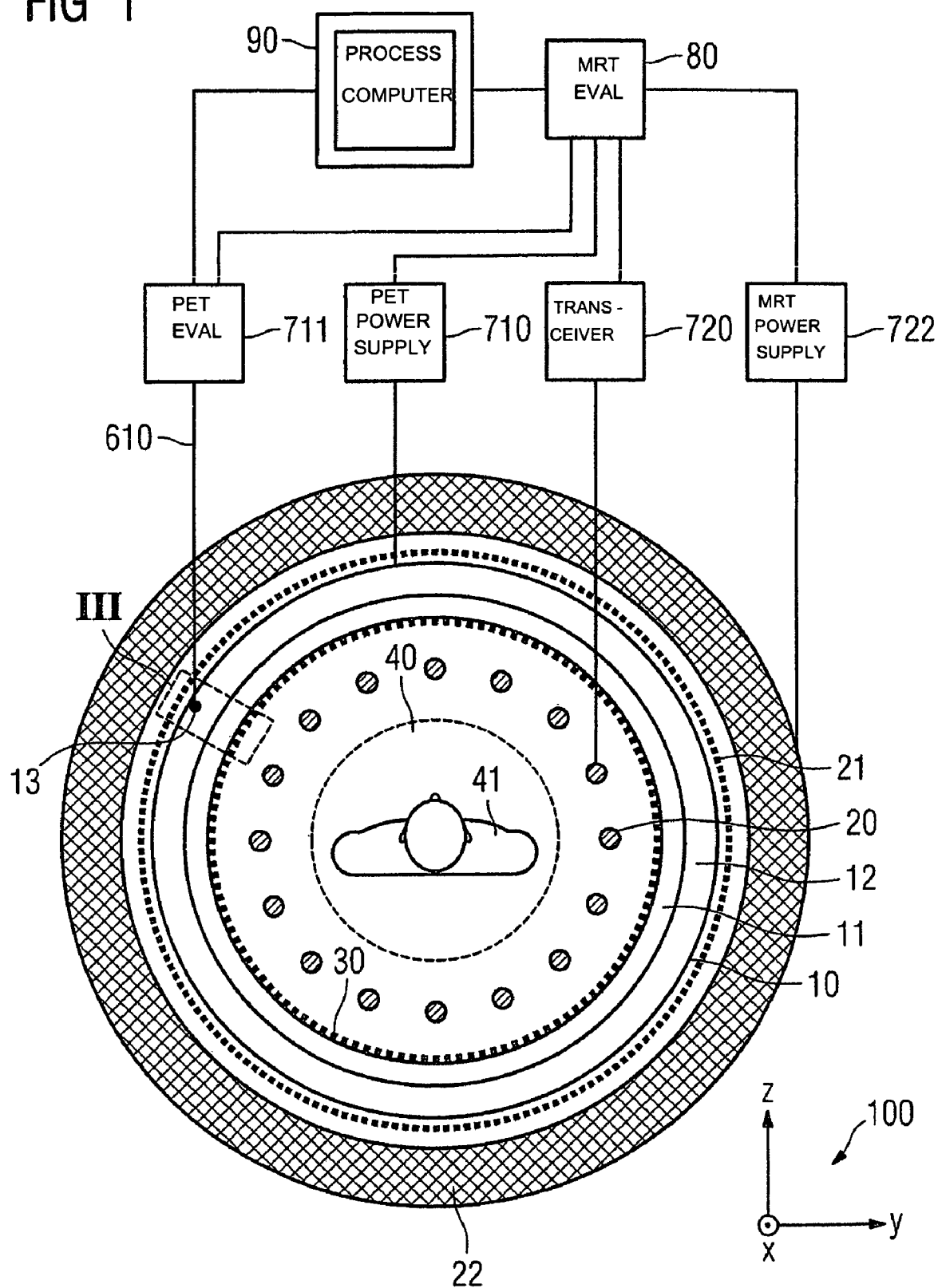

COMBINED POSITRON EMISSION TOMOGRAPHY AND MAGNETIC RESONANCE TOMOGRAPHY UNIT

CROSS REFERENCE TO RELATED APPLICATIONS

This application is based on and hereby claims priority to German Application No. 10 2005 015 070.5 filed on Apr. 1, 2005, the contents of which are hereby incorporated by reference.

BACKGROUND OF THE INVENTION

The invention relates to a combination of positron emission tomography and magnetic resonance tomography units (PET/MRT unit) for imaging an examination object in an examination space. The invention also relates to a method for imaging an examination object in an examination space by a combined positron emission tomography and magnetic resonance tomography unit.

Magnetic resonance tomography (MRT) and positron emission tomography (PET) are nowadays indispensable methods for the accurate diagnosis of many diseases and medical disturbances. It is possible hereby to image affected organs and organ parts exactly in three dimensions and, moreover, to track the physiological and biochemical processes in the affected organs or organ parts down to a molecular plane.

The strength of MRT resides in the ability to image many organs exactly with a very high degree of spatial resolution. By comparison with computed tomography (CT), this method manages here without potentially injurious ionizing radiation. By contrast, the strengths of PET reside chiefly in the functional imaging, that is to say in the imaging of biochemical and physiological processes. However, PET has a comparatively poor spatial resolution of, for example, approximately 5 mm that can no longer be raised without additional radiation loading. By combining the two methods, it is possible to use both the high spatial resolution of MRT and the functional information from PET toward an even more exact diagnosis.

Combined CT and PET measurements are already known to the specialists in the field. In this case, a patient is conveyed directly in sequence through the detector ring of a CT unit and the detector ring of a PET unit. The resulting images are merged in a computer. Similar considerations apply to positron emission tomography and magnetic resonance tomography. In this case, for example, a PET unit can be arranged directly downstream of an MRT unit. The PET is therefore performed after the MRT. Thus, the patient is conveyed, for example, on a couch, from the MRT unit to the PET unit. The two units are consequently separated from one another in space, and the two imaging methods therefore take place independently of one another, consecutively in time.

A diagnostic MRT unit with an examination space is disclosed in DE 44 14 371 C2. The MRT unit in this case comprises a high frequency antenna device and a gradient coil system, the high frequency antenna device being arranged nearer to the examination space than the gradient coil system. A high frequency shield in the shape of the lateral surface of a cylinder is arranged in this case between the gradient coil system and high frequency antenna device.

EP 0 141 383 B1 and EP 0 177 855 B1 specify exemplary embodiments of high frequency antenna devices for MRT units by which a homogeneous magnetic field can be generated in conjunction with a signal sensitivity of uniform nature. Such high frequency antenna devices are also termed bird cage antenna among experts.

SUMMARY OF THE INVENTION

It is one possible object of the invention to specify a combination of a positron emission tomography unit and a magnetic resonance tomography unit that saves space and in which the PET and MRT imaging do not interfere with one another. Furthermore, it is another possible object to specify a method that saves time and in which the PET and MRT imaging do not interfere with one another.

The inventors propose a combined PET/MRT unit for imaging an examination object in an examination space, comprising
a PET unit having
a unit part assigned to the examination space, the unit part comprising a gamma ray detector with an assigned electronics unit for detecting radiation emitted from the examination space of the examination object and converting the radiation into corresponding electric signals, and
a first evaluation unit for evaluating the electric signals for a PET image of the examination object, and
an MRT unit, having
a high frequency antenna device for transmitting high frequency excitation pulses into the examination space and/or for receiving from the examination space magnetic resonance signals from the examination object,
a gradient coil system for generating magnetic gradient fields in the examination space, the high frequency antenna device being arranged nearer to the examination space than the gradient coil system,
a high frequency shield arranged between the gradient coil system and the high frequency antenna device, for decoupling the high frequency antenna device from the gradient coil system, and
a second evaluation unit for evaluating the magnetic resonance signals for an MRT image of the examination object, in which
the PET unit part is arranged between the high frequency shield and the high frequency antenna device, and
the PET unit part is provided, at least on the side facing the high frequency antenna device, with a shielding cover that is caused by the high frequency antenna device and is opaque to high frequency radiation.

By integrating the PET unit part in the MRT unit, it is possible to specify a combined PET/MRT unit that corresponds in terms of dimension approximately to a single MRT unit. Use is made here of the property that the high frequency antenna device is virtually transparent to the PET radiation and therefore passes to the gamma ray detector of the PET unit part virtually without losses. Furthermore, as a result of the shielding cover, on the one hand virtually no high frequency radiation emanating from the high frequency antenna device reaches the gamma ray detector of the PET unit part, and on the other hand virtually no high frequency interfering radiation emanating from the PET unit part passes in the direction of the examination space and thus to the high frequency antenna device. However, the shielding cover is designed to be transparent to the gradient fields, and so a reliable MRT mode is ensured for the unit.

It is particularly advantageous when the PET unit part has an annular cross section, and is arranged concentrically about the examination space. If the gamma ray detector, which particularly has a multiplicity of scintillation detectors, is preferably designed as a closed circular or elliptical ring, this ensures a good spatial resolution for the PET imaging in conjunction with keeping the radiation intensity low, since the entire PET radiation emitted radially by the examination object in the direction of the gamma ray detector can be taken into account for the PET imaging over the angle of 360°.

It is advantageous when the shielding cover has a first, and arranged opposite thereto, a second electrically conductive layer arrangement, the layer arrangements are separated from one another by a dielectric, the layer arrangements comprise conductor tracks that are arranged next to one another and are separated by electrically insulating slots, the slots in the first layer arrangement are arranged offset from the slots in the second layer arrangement, and neighboring conductor tracks are interconnected via bridges conducting high frequency currents. Here, currents induced in the shielding cover by the high frequency antenna device can flow between adjacent conductor tracks essentially via bridges, it being impossible, given a suitable arrangement of the bridges, to induce ring currents, originating from the gradient fields, via a number of conductor tracks, or to induce currents whose resonance frequency is in the region of the operating frequency of the MRT unit. On the other hand, there is essentially no impairment by the bridges of the ability of the gradient fields of the gradient coil system to permeate the shielding cover.

It is advantageous in this case when at least a portion of the bridges is formed by pieces of metal foil. It is thereby possible to adapt the shielding cover flexibly to the shape of the PET unit starting from a slotted basic design.

It is advantageous, furthermore, when at least a portion of the bridges is formed by capacitors. The capacitor design is selected in this case such that they have a large impedance for the operating frequency of the gradient coil system, while their impedance is negligible for operating frequencies of the high frequency antenna device. It is possible thereby to avoid closed circuits in the shielding cover that are induced by gradient fields and can be formed over a number of conductor tracks.

It is possible with particular advantage for the first evaluation unit to be connected to the electronics unit of the PET unit part via at least one signal line running inside and outside the PET unit part, and for a part of the signal line that runs inside the PET unit part to be provided with a filter, in particular with a bandpass filter or else with a cascade of a highpass filter and a notch filter. It is necessary in, this case with reference to the bandpass filter to select the lower cutoff frequency such that the strong low-frequency gradient signals cannot pass via the signal line into the PET unit part shielded against high frequency radiation. However, a sufficiently deep spectral component of the PET signal should be able to pass outward to the first evaluation unit. The upper limit of the bandpass filter is to be selected such that the higher frequency spectral components of the PET signals precisely do not yet interfere with the high frequency signals of the MRT unit. Use is made for the configuration with the cascade of a highpass filter and a notch filter of the fact that the high frequency signals of the MRT unit are of a very narrowband nature with a bandwidth of for example, 0.5 MHz and a center frequency of 64 MHz, Here, the notch filter is to be tuned accurately to the frequencies of the high frequency signals of the MRT unit. The cutoff frequency of the highpass filter is, in addition, to be selected such that the strong low frequency gradient signals cannot pass via the signal line into the PET unit part shielded against high frequency radiation, it being required That a sufficiently deep spectral component of the PET signals be able to pass outward to the first evaluation unit.

It is particularly favorable when all the components of the positron emission tomography unit part are made from nonmagnetic material. Inhomogeneities in the magnetic field inside the combined PET/MRT unit and, in particular, inside the examination space are thereby avoided.

It is also advantageous when the shielding cover is made from nonmagnetic material. Inhomogeneities in the magnetic field inside the combined PET/MRT unit and, in particular, inside the examination space are thereby likewise avoided.

It is particularly advantageous when the electronics unit of the PET unit part is provided with at least one protection diode. The at least one protection diode thereby saves the electronics unit, in particular, from being destroyed by the excitation pulses emitted by the high frequency antenna device of the MRT unit, which can have high, destructive field strengths.

The method proposed by the inventors is a method for imaging an examination object in an examination space by a combined PET/MRT unit, comprising a PET unit having
  a unit part that is assigned to the examination space and comprises a gamma ray detector with an assigned electronics unit, the detector detecting radiation emitted from the examination space by the examination object, and the electronics unit converting the detected radiation into corresponding electric signals, and
a first evaluation unit that evaluates the electric signals for a PET image of the examination object and
an MRT unit that
  has a high frequency antenna device that transmits excitation pulses into the examination space and/or receives from the examination space magnetic resonance signals from the examination object,
  has a gradient coil system that generates magnetic gradient fields in the examination space, the high frequency antenna device being arranged nearer to the examination space than the gradient coil system,
  has a high frequency shield that is arranged between the gradient coil system and the high frequency antenna device and decouples the high frequency antenna device from the gradient coil system, and
  has a second evaluation unit that evaluates the magnetic resonance signals for an MRT image of the examination object, in which
the first evaluation unit does not evaluate electric signals for a PET image of the examination object at least for the duration of each excitation pulse (emitted by the high frequency antenna device), in which
the PET unit part is arranged between the high frequency shield and the high frequency antenna device, and
the PET unit part is provided, at least on the side facing the high frequency antenna device, with a shielding cover that is caused by the high frequency antenna device and is opaque to high frequency radiation.

The fact that the first evaluation unit does not evaluate measured PET signals at least for the duration of each excitation pulse emitted by the high frequency antenna device ensures that the signals received by the evaluation unit also actually stem from PET radiation and not from high frequency interfering radiation emanating from the high frequency antenna device of the MRT unit. This ensures a reliable PET mode of the unit. Moreover, the same advantages are afforded for the method as for the PET/MRT unit.

It is particularly advantageous when the electronics unit of the PET unit part is not supplied with energy for the duration of each excitation pulse emitted by the high frequency antenna device. It is thereby possible to achieve a reduction in the power loss of the PET unit part.

It is, moreover, also advantageous when the electronics unit of the PET unit part is switched into a standby mode for the duration of each excitation pulse emitted by the high frequency antenna device. In the standby mode, that is to say in the energy saving mode of readiness, a reduction in the power loss of the PET unit part can be achieved, on the one hand, and the PET unit part can, on the other hand, respond quickly and switch into recording mode without a great delay.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 1 shows the schematic of a combined positron emission tomography and magnetic resonance tomography unit, FIG. 2 a) shows a shielding cover in cross section with bridges made from pieces of metal foil, FIG. 2 b) shows a plan view of a detail of the shielding cover with bridges made from pieces of metal foil and capacitors.

DETAILED DESCRIPTION OF THE PREFERRED EMBODIMENT

Figure 2A:
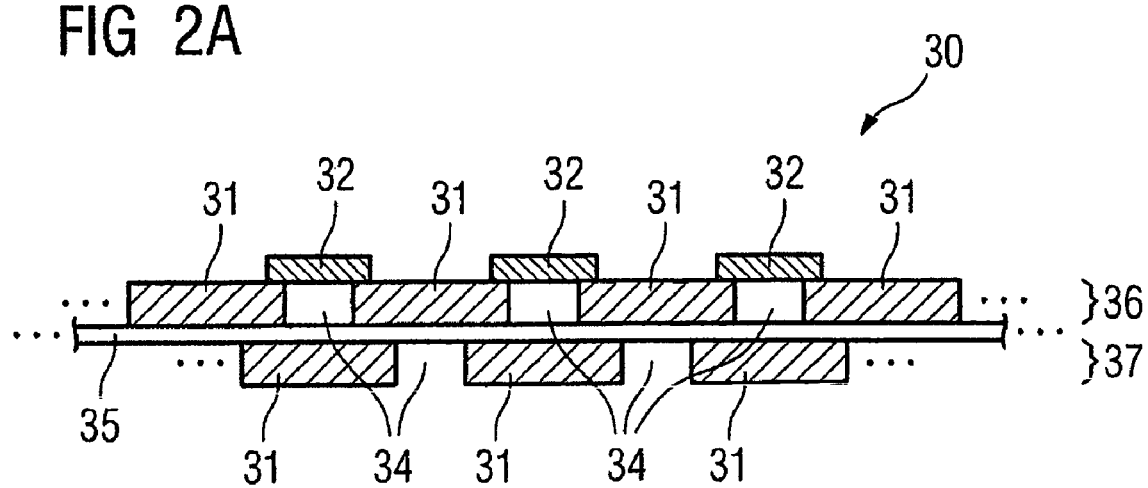

Reference will now be made in detail to the preferred embodiments of the present invention, examples of which are illustrated in the accompanying drawings, wherein like reference numerals refer to like elements throughout. Mutually corresponding parts are provided with the same reference symbols in FIGS. 1 to 4.

FIG. 1 is a schematic of a cross section of a combined PET/MRT unit for imaging an examination object 41 in an examination space 40. The combined PET/MRT unit is composed of an MRT unit and a PET unit with an integrated PET unit part 10.

For the sake of clarity, the obligatory coils in an MRT unit, which generate a fundamental magnetic field in the examination space 40 are not illustrated. In order to generate independent, mutually perpendicular magnetic field gradients of directions x, y, z in accordance with a coordinate system 100, an MRT unit comprises a gradient coil system 22, which is illustrated here only in a simplified schematic fashion. In addition, the MRT unit is assigned a high frequency antenna device 20 for generating excitation pulses in the examination space 40, and/or for receiving magnetic resonance signals from the examination object 41 from the examination space 40. The embodiment of the high frequency antenna device 20 that is illustrated here is formed from a number of antenna rods. Sixteen rods are indicated in FIG. 1 as an example. Such a type of high frequency antenna device is also denoted as a bird cage antenna. Furthermore, a high frequency shield 21 in the shape of the lateral surface of a cylinder and intended, in particular, for the electromagnetic decoupling of the high frequency antenna device 20 from the gradient coil system 22 is indicated between the gradient coil system 22 and high frequency antenna device 20. The high frequency shield 21 is designed in such a way that it is transparent in the low frequency region for the signals generated by the gradient coil system 22, and is opaque in the high frequency region to the signals generated by the high frequency antenna device 20.

The PET unit part 10 comprises a gamma ray detector 11 with the aid of which the PET radiation emitted by the examination object 41 can be detected, and a corresponding electric signal can be generated with the aid of an assigned electronics unit 12. In addition, the PET unit part 10 is of annular configuration and arranged concentrically about the examination space 40. A multiplicity of scintillation detectors 111 (See FIG. 3) facing the examination space 40, for example, can be used as gamma ray detector 11. A shielding cover 30 that is opaque to high frequency radiation can be fitted on the side of the PET unit part 10 facing the high frequency antenna device 20. The shielding cover 30 is designed in such a way that, on the one hand, virtually none of the high frequency radiation emanating from the high frequency antenna device 20 reaches the PET unit part 10 and, on the other hand, virtually none of the high frequency interfering radiation emanating from the PET unit part 10 passes in the direction of the examination space 40 and thus to the high frequency antenna device 20. The shielding cover 30 is, however, of transparent design with reference to the gradient fields.

The electric PET signals pass to an evaluation unit 711 that is connected via a signal line 610 to a connection 13 of the PET unit part 10. The evaluation unit 711 has a process computer with the aid of which PET images are obtained from the electric PET signals. The supply of energy to the PET unit part 10 is ensured by a switch-mode power supply unit 710 that is connected to the PET unit part 10, in particular to the electronics unit 12 of the PET unit part 10. The detail denoted by III emerges more clearly from FIG. 3.

The MRT unit is operated via a further evaluation unit 80, likewise having a process computer. The high frequency antenna device 20 is connected to the evaluation unit 80 via a high frequency transceiver unit 720. Under the control of the evaluation unit 80, it is in this case excited by the transceiver unit 720 to emit excitation pulses. Magnetic resonance signals received thereupon from the high frequency antenna device 20 are then transmitted to the evaluation unit 80 in turn via the transceiver unit 720, if appropriate in a fashion amplified by an amplifier integrated in the transceiver unit 720. The evaluation unit 80 then obtains an MRT image from the magnetic resonance signal.

In accordance with the exemplary embodiment in FIG. 1, the gradient coil system 22 is supplied with current, likewise under the control of the evaluation unit 80, with the aid of a power supply 722 connected to the gradient coil system 22. There is also a connection between the first evaluation unit 711 assigned to the PET unit part 10 and the second evaluation unit 80, assigned to the MRT unit, via which the first evaluation unit 711 receives signals transmitted by the second evaluation 80 and which interrupt the evaluation in the first evaluation unit 711 over the duration of an excitation pulse. So that, if appropriate, the switch-mode power supply unit 710, which in particular supplies energy to the electronics unit 12 of the PET unit part 10, can, moreover, likewise be driven depending on how the MRT unit is driven, it is itself also connected to the evaluation unit 80.

The PET and MRT tomograms obtained with the aid of the evaluation units 711 and 80 are transmitted to a process computer 90 that preferably has a display screen output by which the tomograms can be superimposed by computation and output as a combined PET/MRT image.

Figure 2B:
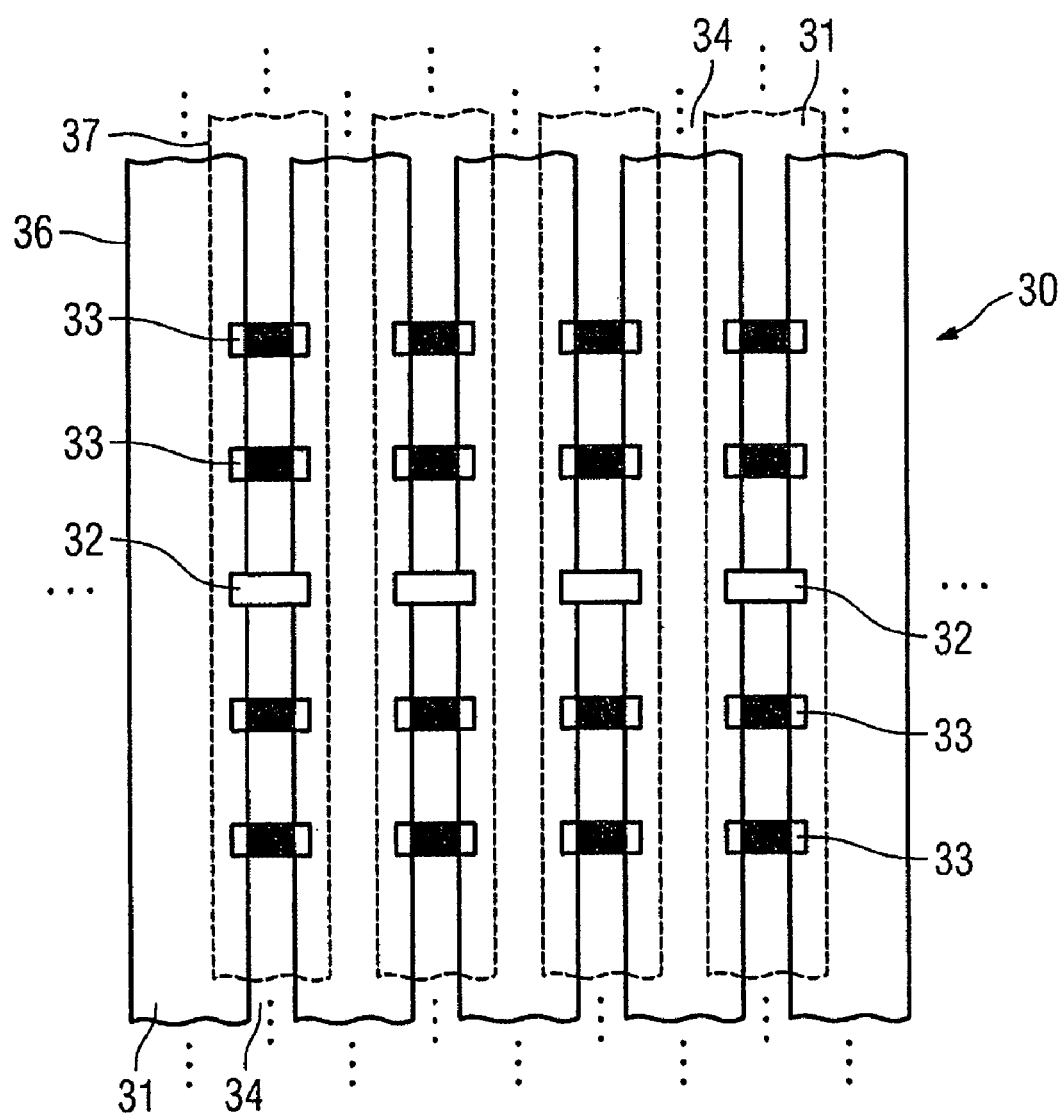

A part of the shielding cover 30 is illustrated in cross section in FIG. 2a. FIG. 2b shows a plan view of a detail of the shielding cover. The shielding cover 30 comprises two metallic layer arrangements 36 and 37 (upper and lower), in particular made from copper, that are respectively configured from conductor tracks 31 arranged next to one another. The conductor tracks 31 are separated in this case by electrically insulating slots 34. The two layer arrangements 36 and 37 are applied to a dielectric 35 arranged between the layer arrangements, in particular one made from epoxy or Teflon material reinforced with glass fiber fabric. Here, the two layer arrangements 36 and 37 are arranged relative to one another in such a way that their conductor tracks 31 and slots 34 are arranged in an offset fashion.

FIG. 2*b* shows a plan view of a detail of the shielding cover 30. The conductor tracks 31 depicted are designed here to be parallel to one another, by way of example. In this case, the upper layer arrangement 36 constitutes the layer arrangement 36 facing the high frequency antenna device 20. The neighboring conductor tracks 31 of the upper layer arrangement 36 are interconnected via bridges 32, 33 conducting high frequency currents. Element 32 is also shown in FIG. 2*a*. Currents induced by the high frequency antenna device 20 in the upper layer arrangement 36 can flow between neighboring conductor tracks 31 via the bridges 32, 33. A portion of the bridges 32, 33 can be designed as metal foils that electrically interconnect respectively neighboring conductor tracks 31. The electrical connections can be produced, for example, by soldering, spot welding or else by being pressed on. So that the currents induced by the gradient coil system 22 in the upper layer arrangement 36 do not encounter any closed current paths of a number of conductor tracks 31, two bridges 32, 33 are designed as capacitors, in particular ceramic capacitors. The dimensioning of the capacitors of the bridge 33 is selected in such a way that the capacitors of bridge 33 offer a negligible impedance to the high frequency currents induced by the high frequency antenna device 201 while the impedance for the currents induced by the gradient coil system 22 is very high. The arrangement illustrated in FIG. 2*b* of the bridges 32, 33 is intended merely as an illustration. When selecting the arrangement of the bridges 32, 33, it is to be ensured7 in particular, that no ring currents induced by the gradient coil system 22 can flow via a number of conductor tracks 31, and also that no currents whose resonance frequency is in the region of the operating frequency of the magnetic resonance unit can flow. The lower layer arrangement 37 is not provided with bridges in the exemplary embodiment depicted. However, it is also conceivable for the conductor tracks 31 of the lower layer arrangement 37 likewise to be connected with the aid of bridges 32, 33 in accordance with the upper layer arrangement 36. For the sake of clarity, the dielectric 35 is not depicted in FIG. 2*b*. In a further exemplary embodiment (not illustrated further here), of the shielding cover 30, the latter has only a single layer arrangement 36 provided with bridges 32, 33. The shielding and high frequency properties of this design do not quite reach the good shielding and high frequency properties of the design illustrated in FIGS. 2*a* and 2*b*. However, such a design is simple and can be produced cost effectively.

Figure 3:
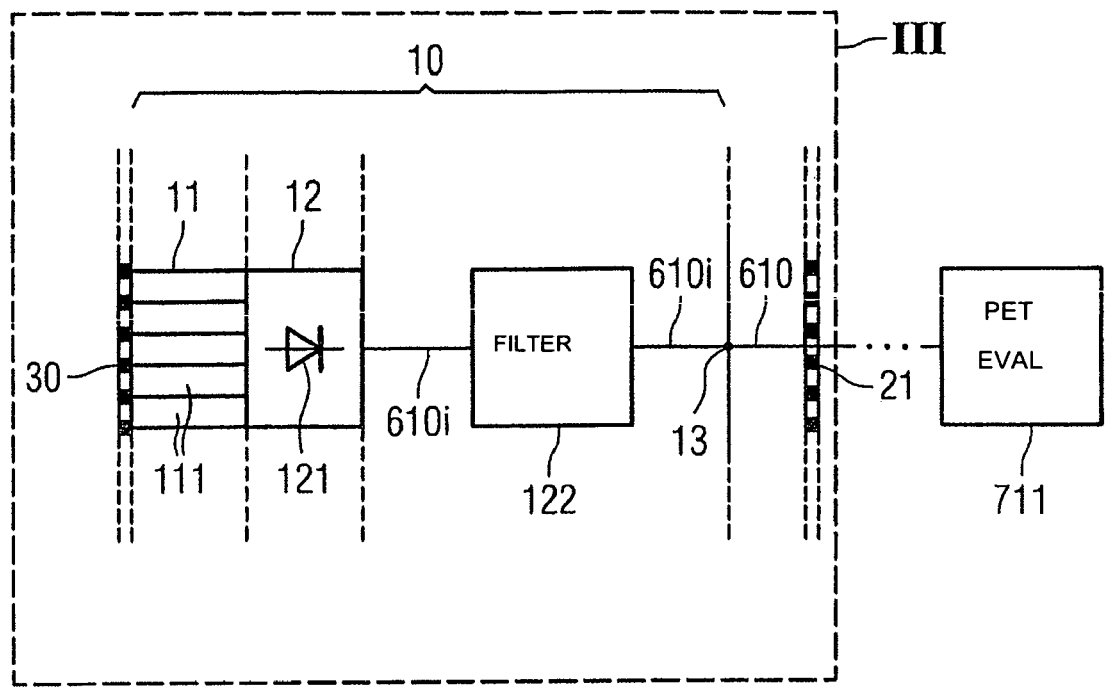
FIG. 3 shows a detail of the combined PET/MRT unit in accordance with FIG. 1.

FIG. 3 illustrates the detail denoted by III in FIG. 1. The PET unit part 10 is connected in this case to the evaluation unit 711 via the connection 13 by the signal line 610. The high frequency shield 21 is illustrated between the evaluation unit 711 and PET unit part 10. The gamma ray detector 11 is arranged with an associated electronics unit 12 inside the PET unit part 10. The PET unit part 10 is provided with the shielding cover 30 (illustrated schematically here) on the detector side. The gamma ray detector 11 has a number of scintillation detectors 111 arranged next to one another. To provide protection against destruction by the relatively high field strengths that originate from the high frequency antenna device 20, the electronics unit 12 is provided with at least one protection diode 121. By a signal line 610*i*, the electronics unit 12 is connected to the connection 30 of the PET unit part 10 via a filter 122, in particular via a bandpass filter or via a filter designed as a cascade of a highpass filter and a notch filter.

Figure 4:
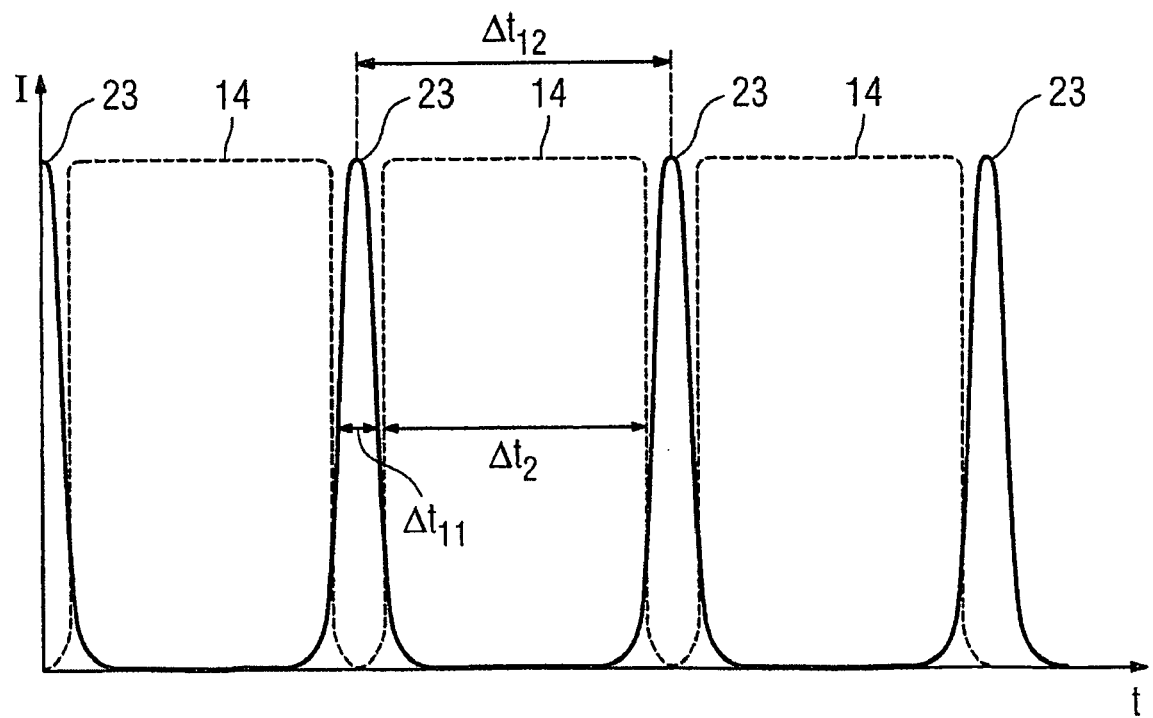
FIG. 4 shows a schematic of the temporal sequence during operation of the combined PET/MRT unit for the combined PET/MRT imaging method.

FIG. 4 is a schematic of the temporal sequence during operation of the PET/MRT unit for the combined PET/MRT imaging method. The abscissa forms the time axis t, while the ordinate represents the intensity I of the excitation pulse 23. The units are arbitrary. Also plotted in the diagram is a dashed line 14 that is intended to reproduce the operating state of the evaluation unit 711 assigned to the PET unit and, if appropriate, of the power supply unit 710 assigned to the PET unit part 10. The line 14 illustrates the time segments during which the evaluation unit 711 evaluates PET signals for a PET image and, if appropriate, the time segments during which the power supply unit 710 supplies the PET unit part 10, in particular the electronics unit 12, with energy. Throughout the pulse duration $\Delta t11$ of an excitation pulse 23, the evaluation unit 711 does not evaluate PET signals, and the power supply unit 710 is, if appropriate switched off or switched to standby. Between two excitation pulses 23, which have a temporal spacing of $\Delta t12$, the evaluation unit 711 is in the evaluation mode for the time period $\Delta t2$, where $\Delta t2 < \Delta t12$, and the power supply unit 710 is switched on, the PET unit part 10, in particular the electronics unit 12, being supplied with energy. In accordance with FIG. 1, the evaluation unit 711 and, if appropriate, the power supply unit 710 are controlled as a function of the pulse sequence of the MRT unit by virtue of the fact that the evaluation unit 711 assigned to the PET unit part 10 and, if appropriate, the power supply unit 710 are controlled by the evaluation unit 80, which likewise controls the transceiver unit 720 assigned to the MRT unit.

Thus, a PET image and an MRT image can be recorded simultaneously with the aid of the combined PET/MRT imaging method. This combined recording lasts just as long as the recording of an MRT image on its own, since the period $\Delta t12$ that is present in any case for the MRT imaging can be used between two excitation pulses 23 in order to record a PET image.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

What is claimed is:

1. A combined positron emission tomography and magnetic resonance tomography unit for imaging an examination object in an examination space, comprising:
   a positron emission tomography unit comprising:
      a unit part assigned to the examination space, the unit part comprising a gamma ray detector with an assigned electronics unit for detecting radiation emitted from the examination space by the examination object and converting the radiation into corresponding electric signals, and
      a first evaluation unit for evaluating the electric signals for a positron emission tomography image of the examination object, and
   a magnetic resonance tomography unit, comprising:
      a high frequency antenna device emitting high frequency excitation pulses and transmitting the excitation pulses to the examination space and/or receiving from the examination space magnetic resonance signals from the examination object, a gradient coil system for generating magnetic gradient fields in the examination space, the high frequency antenna device being arranged nearer to the examination space than the gradient coil system, a high frequency shield arranged between the gradient coil system and the high frequency antenna device, for decoupling the high frequency antenna device from the gradient coil system, and a second evaluation unit for evaluating the magnetic resonance signals for a magnetic resonance tomography image of the examination object; and a shielding cover positioned between the positron emission tomography unit part and the high frequency antenna device, the shielding cover being opaque to high frequency radiation, wherein both the positron emission tomography unit part and the shielding cover are provided within longitudinal extents of the examination space, and the positron emission tomography unit part is positioned between the high frequency shield and the high frequency antenna device.

2. The combined positron emission tomography and magnetic resonance tomography unit as claimed in claim 1, wherein the positron emission tomography unit part:

has an annular cross section, and is arranged concentrically about the examination space.

3. The combined positron emission tomography and magnetic resonance tomography unit as claimed in claim 2, wherein the shielding cover has a first, and arranged opposite thereto, second electrically conductive layers, the first and second electronically conductive layers are separated from one another by a dielectric, the layers comprise conductor tracks that are arranged next to one another and are separated by electrically insulating slots, the slots in the first layer electrically conductive are arranged offset from the slots in the second electrically conductive layer, and neighboring conductor tracks are interconnected via bridges to conduct high frequency currents.

4. The combined positron emission tomography and magnetic resonance tomography unit as claimed in claim 3, wherein at least some of the bridges are respectively formed of pieces of metal foil.

5. The combined positron emission tomography and magnetic resonance tomography unit as claimed in claim 4, characterized in that at least a portion of the bridges is formed by capacitors.

6. The combined positron emission tomography and magnetic resonance tomography unit as claimed in claim 5 wherein the first evaluation unit is connected to the electronics unit of the positron emission tomography unit part via at least one signal line running inside and outside of the positron emission tomography unit part, and a bandpass filter is provided where the signal line runs inside the positron emission tomography unit part.

7. The combined positron emission tomography and magnetic resonance tomography unit as claimed in claim 5 wherein the first evaluation unit is connected to the electronics unit of the positron emission tomography unit part via at least one signal line running inside and outside of the positron emission tomography unit part, and a cascade filter, a high-pass filter or a notch filter is provided where the signal line runs inside the positron emission tomography unit part.

8. The combined positron emission tomography and magnetic resonance tomography unit as claimed in claim 5, wherein all components of the positron emission tomography unit part are made from nonmagnetic material.

9. The combined positron emission tomography and magnetic resonance tomography unit as claimed in claim 8, wherein the shielding cover is made from nonmagnetic material.

10. The combined positron emission tomography and magnetic resonance tomography unit as claimed in claim 1, wherein the shielding cover has first, and arranged opposite thereto, second electrically conductive layers, the first and second electronically conductive layers are separated from one another by a dielectric, the first and second electronically conductive layers comprise conductor tracks that are arranged next to one another and are separated by electrically insulating slots, the slots in the first electrically conductive layer are arranged offset from the slots in the second electrically conductive layer, and neighboring conductor tracks are interconnected via bridges to conduct high frequency currents.

11. The combined positron emission tomography and magnetic resonance tomography unit as claimed in claim 10, wherein at least some of the bridges are respectively formed of pieces of metal foil.

12. The combined positron emission tomography and magnetic resonance tomography unit as claimed in claim 10, wherein at least a portion of the bridges form capacitors.

13. The combined positron emission tomography and magnetic resonance tomography unit as claimed in claim 1 wherein the first evaluation unit is connected to the electronics unit of the positron emission tomography unit part via at least one signal line running inside and outside of the positron emission tomography unit part, and a bandpass filter is provided where the signal line runs inside the positron emission tomography unit part.

14. The combined positron emission tomography and magnetic resonance tomography unit as claimed in claim 1, wherein the first evaluation unit is connected to the electronics unit of the positron emission tomography unit part via at least one signal line running inside and outside of the positron emission tomography unit part, and a cascade filter, a high-pass filter or a notch filter is provided where the signal line runs inside the positron emission tomography unit part.

15. The combined positron emission tomography and magnetic resonance tomography unit as claimed in claim 1 wherein all components of the positron emission tomography unit part are made from nonmagnetic material.

16. The combined positron emission tomography and magnetic resonance tomography unit as claimed in claim 1 wherein the shielding cover is made from nonmagnetic material.

17. The combined positron emission tomography and magnetic resonance tomography unit as claimed in claim 1 wherein the electronics unit of the positron emission tomography unit part is provided with at least one protection diode to protect the electronics unit from the excitation pulses emitted by the high frequency antenna device of the magnetic resonance tomography unit.

18. A method for imaging an examination object in an examination space using a combined positron emission tomography and magnetic resonance tomography unit, the method comprising:

detecting radiation emitted from the examination space by the examination object and converting the radiation into corresponding electric signals using a positron emission tomography unit part assigned to the examination space, the unit part comprising a gamma ray detector with an assigned electronics unit; evaluating the electric signals for a positron emission tomography image of the examination object; emitting high frequency excitation pulses and transmitting the excitation pulses to the examination space and/or receiving from the examination space magnetic resonance signals from the examination object using a high frequency antenna device;

generating magnetic gradient fields in the examination space using a gradient coil system, the high frequency antenna device being arranged nearer to the examination space than the gradient coil system decoupling the high frequency antenna device from the gradient coil system using a high frequency shield arranged between the gradient coil system and the high frequency antenna device;

evaluating the magnetic resonance signals for a magnetic resonance tomography image of the examination object; and shielding the positron emission tomography unit part and the high frequency antenna device using a shielding cover positioned between the positron emission tomography unit part and the high frequency antenna device, the shielding cover being opaque to high frequency radiation, wherein both the positron emission tomography unit part and the shielding cover are provided within longitudinal extents of the examination space, and the positron emission tomography unit part is positioned between the high frequency shield and the high frequency antenna device.

19. The method as claimed in claim 18, wherein the electronics unit of the positron emission tomography unit part is not supplied with energy during the emission of each excitation pulse by the high frequency antenna device.

20. The method as claimed in claim 18, wherein the electronics unit of the positron emission tomography unit part is switched into a standby mode during the emission of each excitation pulse by the high frequency antenna device.

* * * * *